(12) United States Patent
Danter et al.

(10) Patent No.: US 8,252,800 B2
(45) Date of Patent: *Aug. 28, 2012

(54) PROTEIN TYROSINE KINASE INHIBITORS

(76) Inventors: Wayne R. Danter, London (CA);
Martyn Brown, Toronto (CA); George Ma, Toronto (CA); Ghenadie Rusu, Toronto (CA); Jianhua Zhong, Toronto (CA); Natalie Lazarowych, Toronto (CA); Stephen Houldsworth, Toronto (CA)

( * ) Notice: Subject to any disclaimer, the term of this patent is extended or adjusted under 35 U.S.C. 154(b) by 472 days.

This patent is subject to a terminal disclaimer.

(21) Appl. No.: 12/510,862

(22) Filed: Jul. 28, 2009

(65) Prior Publication Data

US 2009/0298855 A1    Dec. 3, 2009

Related U.S. Application Data

(63) Continuation of application No. 10/522,944, filed as application No. PCT/CA03/01162 on Jul. 31, 2003, now Pat. No. 7,585,866.

(51) Int. Cl.
*C07D 401/14* (2006.01)
*A61K 31/506* (2006.01)

(52) U.S. Cl. ........ 514/256; 514/316; 514/318; 544/296; 544/333; 546/187

(58) Field of Classification Search .................. 544/296, 544/333; 546/187; 514/256, 316, 318
See application file for complete search history.

(56) References Cited

U.S. PATENT DOCUMENTS

| | | | |
|---|---|---|---|
| 5,155,110 A | 10/1992 | Connor et al. | |
| 5,328,914 A | 7/1994 | Hocquaux et al. | |
| 5,409,930 A | 4/1995 | Spada et al. | |
| 5,480,883 A | 1/1996 | Spada et al. | |
| 5,521,184 A | 5/1996 | Zimmermann | |
| 5,543,520 A | 8/1996 | Zimmermann | |
| 5,612,340 A | 3/1997 | Zimmermann | |
| 5,618,829 A | 4/1997 | Takayanagi et al. | |
| 5,646,153 A | 7/1997 | Spada et al. | |
| 5,656,643 A | 8/1997 | Spada et al. | |
| 5,710,158 A | 1/1998 | Myers et al. | |

(Continued)

FOREIGN PATENT DOCUMENTS
EP    0225726    6/1987

(Continued)

OTHER PUBLICATIONS

Traxler, Protein Tyrosine Kinase Inhibitors in Cancer Treatment, Expert Opinion on Therapeutic Patents, 7(6):571-588, 1997.*

(Continued)

*Primary Examiner* — Deepak Rao
(74) *Attorney, Agent, or Firm* — Thomas, Kayden, Horstemeyer & Risley, LLP

(57) ABSTRACT

The present invention relates to compounds of the Formula I, the pharmaceutically acceptable salts and stereoisomers thereof, which inhibit, regulate and/or modulate tyrosine kinase signal transduction, compositions which contain these compounds, and methods of using them to treat tyrosine kinase-dependent diseases and conditions in mammals:

Formula I wherein n is an integer, preferably n is 1;
wherein $R_1$ and $R_2$ are independently selected from the group consisting of:

17 Claims, No Drawings

U.S. PATENT DOCUMENTS

| | | | |
|---|---|---|---|
| 5,714,493 A | 2/1998 | Myers et al. |
| 5,721,238 A | 2/1998 | Heiker et al. |
| 5,736,534 A | 4/1998 | Arnold |
| 5,760,041 A | 6/1998 | Wissner et al. |
| 5,763,470 A | 6/1998 | Tang et al. |
| 5,795,889 A | 8/1998 | Spada et al. |
| RE36,256 E | 7/1999 | Spada et al. |
| 5,932,574 A | 8/1999 | Baker |
| 5,958,935 A | 9/1999 | Davis et al. |
| 6,057,320 A | 5/2000 | Spada et al. |
| 6,069,134 A | 5/2000 | Roth et al. |
| 6,103,728 A | 8/2000 | Tang et al. |
| 6,127,374 A | 10/2000 | Bridges |
| 6,153,617 A | 11/2000 | Bridges |
| 6,169,091 B1 | 1/2001 | Cockerill et al. |
| 6,174,889 B1 | 1/2001 | Cockerill et al. |
| 6,180,636 B1 | 1/2001 | Traxler et al. |
| 6,184,377 B1 | 2/2001 | Gao |
| 6,207,669 B1 | 3/2001 | Cockerill et al. |
| 6,235,746 B1 | 5/2001 | Davis et al. |
| 6,251,911 B1 | 6/2001 | Bold et al. |
| 6,253,168 B1 | 6/2001 | Griffey et al. |
| 6,268,391 B1 | 7/2001 | Dickerson et al. |
| RE37,650 E | 4/2002 | Myers et al. |
| 6,391,874 B1 | 5/2002 | Cockerill et al. |
| 6,432,963 B1 | 8/2002 | Hisamichi et al. |
| 6,525,072 B1 | 2/2003 | Tang et al. |
| 6,528,509 B1 | 3/2003 | Hale et al. |
| 6,562,818 B1 | 5/2003 | Bridges |
| 6,600,037 B1 | 7/2003 | Davis et al. |
| 6,635,641 B2 | 10/2003 | Bender et al. |
| 6,723,726 B1 | 4/2004 | Cockerill et al. |
| 6,828,320 B2 | 12/2004 | Cockerill et al. |
| 7,585,866 B2 * | 9/2009 | Danter et al. ................ 514/256 |
| 2001/0021717 A1 | 9/2001 | Potter et al. |
| 2001/0027205 A1 | 10/2001 | Camden |
| 2001/0041964 A1 | 11/2001 | Grass et al. |
| 2001/0044451 A1 | 11/2001 | Fraley et al. |
| 2001/0047007 A1 | 11/2001 | Fraley et al. |
| 2001/0047364 A1 | 11/2001 | Proctor |
| 2001/0049092 A1 | 12/2001 | Ekins et al. |
| 2001/0051628 A1 | 12/2001 | Huang et al. |
| 2002/0010550 A1 | 1/2002 | Grass et al. |
| 2002/0012641 A1 | 1/2002 | Voorhees et al. |
| 2002/0013334 A1 | 1/2002 | Robl et al. |
| 2002/0013662 A1 | 1/2002 | Grass et al. |
| 2002/0014408 A1 | 2/2002 | Schroeder |
| 2002/0018988 A1 | 2/2002 | Klinck et al. |
| 2002/0028779 A1 | 3/2002 | High et al. |
| 2002/0028826 A1 | 3/2002 | Robl et al. |
| 2002/0042423 A1 | 4/2002 | Richert et al. |
| 2002/0061901 A1 | 5/2002 | Robl et al. |
| 2002/0072526 A1 | 6/2002 | Fraley et al. |
| 2002/0086791 A1 | 7/2002 | Iglesia et al. |
| 2002/0115858 A1 | 8/2002 | Zimmermann et al. |
| 2002/0147214 A1 | 10/2002 | Cockerill et al. |
| 2003/0087881 A1 | 5/2003 | Bridges |
| 2003/0125343 A1 | 7/2003 | Gambacorti-Passerini et al. |
| 2003/0130286 A1 | 7/2003 | Denny et al. |
| 2003/0153755 A1 | 8/2003 | Moffat et al. |
| 2003/0212269 A1 | 11/2003 | Davis et al. |
| 2004/0092747 A1 | 5/2004 | Bender et al. |
| 2004/0102453 A1 | 5/2004 | Buerger et al. |
| 2004/0224968 A1 | 11/2004 | Seidelmann et al. |
| 2004/0235786 A1 | 11/2004 | Orr |
| 2005/0192884 A1 | 9/2005 | Raines |

FOREIGN PATENT DOCUMENTS

| | | |
|---|---|---|
| EP | 600832 | 11/1993 |
| EP | 0722937 | 1/1996 |
| JP | 05058894 | 3/1993 |
| JP | 11080131 | 3/1999 |
| WO | WO 96/09294 | 3/1996 |
| WO | WO 97/03069 | 1/1997 |
| WO | WO 97/13760 | 4/1997 |
| WO | WO 99/09016 | 2/1999 |
| WO | WO 00/18740 | 4/2000 |
| WO | WO 00/50032 | 8/2000 |
| WO | WO 01/12227 | 2/2001 |
| WO | WO 01/25220 | 4/2001 |
| WO | WO 01/53274 | 7/2001 |
| WO | WO 01/70741 | 9/2001 |
| WO | WO 02/22597 | 3/2002 |
| WO | WO 00/61186 | 10/2002 |
| WO | WO 2004/011456 | 2/2004 |

OTHER PUBLICATIONS

Simone, Oncology: Introduction, Cecil Textbook of Medicine, 20th Edition, vol. 1, pp. 1004-1010, 1996.*

Johnson et al., Relationships between drug activity in NCI preclinical in vitro and in vivo models and early clinical trials, British Journal of Cancer (2001) 64(10): 1424-1431.*

Gura, Systems for Identifying New Drugs Are Often Faulty, Cancer Models, Science, vol. 278, No. 5340, pp. 1041-1042, Nov. 1997.*

Monks, et al. J. Natl. Cancer Institute 83(11):757-66, 1991 "Feasibility of a high-flux anticancer drug screen using a diverse panel of cultured human tumor cell lines".

Bolen Oncogene, 8:2025-2031 (1993).

Plowman, et al., "Receptor Tyrosine Kinases as Targets for Drug Intervention", DN&P 7(6):334-339, 1994.

Eliel, Ernest L., Wilen, Samuel H., Mander, Lewis N., "Stereochemistry of Organic Compounds"; A Wiley-Interscience Publication, John Wiley & Sons, Inc., pp. 1119-1190, (1993).

Attoub, et al.; The c-kit Tyrosine Kinase Inhibitor STI571 for Colorectal Cancer Therapy; Cancer Research 623, 4879-4883, Sep. 1, 2002.

Decaudin, et al.; In vivo Efficacy of STI571 in Xenografted Human Small Cell Lung Cancer Alone or Combined with Chemotherapy; Int. J. Cancer: 113, 849-856; 2005.

Le Coutre, et al.; In Vivo Eradication of Human BCR/ABL-Positive Leukemia Cells With an ABL Kinase Inhibitor; Journal of the National Cancer Institute; vol. 91, No. 2; Jan. 20, 1999.

Lev, et al.; Inhibition of Platelet-Derived Growth Factor Receptor Signaling Restrictions the Growth of Human Breast Cancer in the Bone of Nude Mice; Clinical Cancer Research; vol. 11, 306-315, Jan. 1, 2005.

Zwick, et al.; Receptor Tyrosine Kinases as Targets for Anticancer Drugs; Trends in Molecular Medicine; vol. 8, No. 1; Jan. 2002; 17-23.

Krause, et al.; Tyrosine Kinases as Targets for Cancer Therapy; New England Journal of Medicine; 353;2; Jul. 14, 2005; 172-187.

NSC No. 84442-R; Screening Data Summary, Developmental Therapeutics Program, Division of Cancer Treatment, National Cancer Institute; See pp. 2 and 3; Jun. 1, 1967.

Eliel, Ernest L., et al. "Stereochemiistry of Organic Compounds", A Wiley-Intersecince publication, John Wiley & Sons., pp. 1119-1190, 1994.

Monks, et al. "Feasbility of a high-flux anticancer drug screen using a diverse panel of culterued human tumor cell lines" Natl. Cancer Inst. 83(11): 757-66, 1991.

* cited by examiner

PROTEIN TYROSINE KINASE INHIBITORS

CROSS-REFERENCE TO RELATED APPLICATION

This application claims priority to copending U.S. application having Ser. No. 10/522,944, filed Jul. 28, 2005, which is a national phase entry (371) of PCT/CA03/01162, filed Jul. 31, 2003, which claims priority to U.S. provisional application having Ser. No. 60/399,408, each entirely incorporated herein by reference.

FIELD OF THE INVENTION

The present invention relates to compounds which inhibit, regulate and/or modulate tyrosine kinase signal transduction, compositions which contain these compounds, and methods of using them to treat tyrosine kinase-dependent diseases and conditions in mammals.

BACKGROUND OF THE INVENTION

Throughout this application, various references are cited in parentheses to describe more fully the state of the art to which this invention pertains. The disclosure of these references are hereby incorporated by reference into the present disclosure.

Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. Approximately, 20 different subfamilies of receptor-type tyrosine kinases have been identified. One tyrosine kinase subfamily is comprised of EGFR, HER2, HER3, and HER4. Ligands of this subfamily of receptors include epithelial growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. The FLK family is comprised of the kinase insert domain receptor (KDR), fetal liver kinase-1 (FLK-1), fetal liver kinase-4 (FLK-4) and the fms-like tyrosine kinase-1 (flt-1) (Plowman et al., DN&P 7(6):334-339, 1994, which is hereby incorporated by reference).

The non-receptor type of tyrosine kinases are also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis (Bolen Oncogene, 8:2025-2031 (1993), which is hereby incorporated by reference).

Both receptor-type and non-receptor type tyrosine kinases are implicated in cellular signalling pathways leading to numerous pathogenic conditions, including a variety of cancers. For example, the Bcr-Abl tyrosine kinase is the constitutive abnormal tyrosine kinase created by the Philadelphia chromosome abnormality in chronic myeloid leukemia (CML). Inappropriate Bcr-Abl activity is also demonstrated in murine myeloid cells as well as Bcr-Abl positive leukemia lines derived from CML patients in blast crisis.

A variety of tyrosine kinase inhibitors have been developed for the treatment of different types of clinical conditions. See for example U.S. Pat. Nos. 5,543,520 and 5,521,184.

It is therefore desirable to identify additional compounds which specifically inhibit, regulate and/or modulate the signal transduction of tyrosine kinases and in particular those tyrosine kinases involved in various malignancies in order to develop novel strategies for treatment.

SUMMARY OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as cancer and tumor growth, and the like in mammals.

More particularly, the present invention relates to compounds that are capable of inhibiting, modulating and/or regulating signal transduction of both receptor-type and non-receptor type tyrosine kinases. The compounds are novel protein tyrosine kinase inhibitors useful in the treatment of a variety of malignancies involving inappropriate tyrosine kinase activity.

One embodiment of the present invention is illustrated by a compound of Formula I, and the pharmaceutically acceptable salts and stereoisomers thereof:

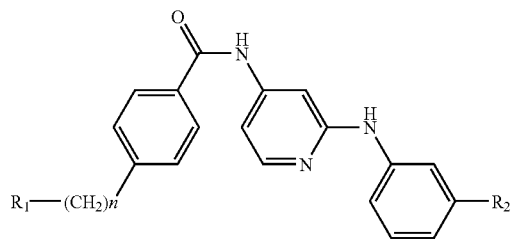

Formula I wherein n is an integer, preferably n is 1;

wherein $R_1$ and $R_2$ are independently selected from the group consisting of:

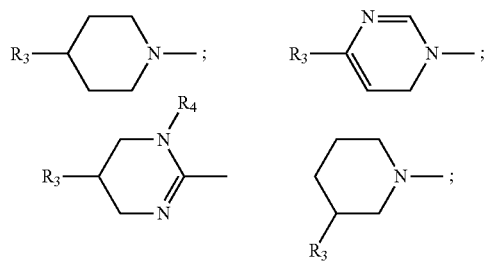

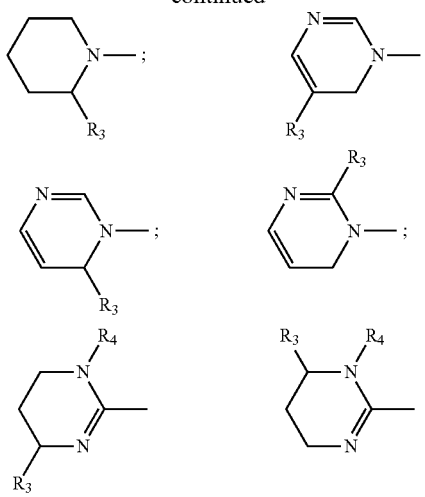

wherein $R_3$ is selected from the group consisting of H; alkyl; alkenyl; alkynyl; halogen; aryl; heteroaryl containing N, O, or S; the aryl and heteroaryl may be further substituted with halogen, an alkyl, alkenyl, and alkynyl; $NZ_1Z_2$, wherein $Z_1$ and $Z_2$ are independently selected from the group consisting of H and alkyl; and (CO)Y wherein Y is selected from the group consisting of H, alkyl, alkenyl, alkynyl, aryl, heteroaryl containing N, O, or S, and the aryl and heteroaryl may be further substituted with halogen, alkyl, alkenyl, and alkynyl; and wherein $R_4$ is selected from the group consisting of H and alkyl.

In one aspect of the present invention, the compound is represented as formula II:

Formula II

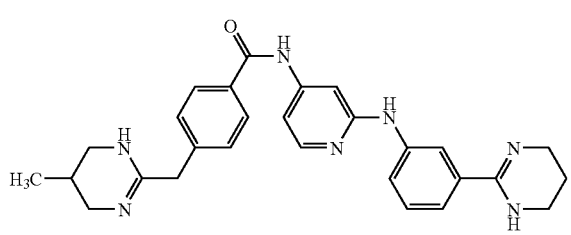

In a further aspect of the present invention, the compound is represented as formula III:

Formula III

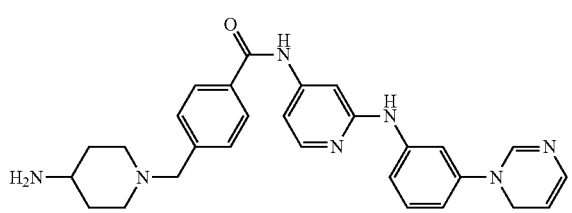

In a further aspect of the present invention, the compound is represented as formula IV:

Formula IV

According to another aspect of the present invention is a pharmaceutical composition which is comprised of a compound in accordance with formula I together with a pharmaceutically acceptable carrier.

According to another aspect of the present invention is a pharmaceutical composition which is comprised of a compound in accordance with formula II or formula II together with a pharmaceutically acceptable carrier.

According to another aspect of the present invention is a method of treating or preventing cancer involving inappropriate tyrosine kinase activity in a mammal in need of such treatment which is comprised of administering to the mammal a therapeutically effective amount of a compound of formula I, II, III or IV, or mixtures thereof.

According to another aspect of the present invention is a method of treating cancer or preventing cancer using a composition comprising a compound of formula I, II, III or IV, or mixtures thereof, wherein the cancer is selected from cancers of the breast, leukemias, melanoma, stomach, colon, CNS, ovarian and prostate and those listed in Table I.

According to still another aspect of the present invention is a method of treating or preventing cancer using a composition comprising a compound of formula I, II, III or IV, or mixtures thereof, wherein the cancer is chronic myelogic leukemia (CML).

According to another aspect of the present invention is a method of treating or preventing a tyrosine kinase-dependent disease or condition which comprises administering a therapeutically effective amount of a compound selected from the group consisting of formula I, formula II, formula II, formula IV and mixtures thereof.

According to yet another aspect of the present invention is a process for making a pharmaceutical composition which comprises combining a compound of formula I, II, III and/or IV with a pharmaceutically acceptable carrier.

According to another aspect of the present invention is the use of a compound of formula I, II, III and/or IV in a medicament for the treatment of a disease or condition involving inappropriate tyrosine kinase activity.

According to still a further aspect of the present invention is composition comprising a compound of formula I further comprising a second compound selected from the group consisting of an estrogen receptor modulator, an androgen receptor modulator, retinoid receptor modulator, a cytotoxic agent, an anti-proliferative agent, a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, and troponin-1, tamoxifen and raloxifene.

According to a further aspect of the present invention is a method of treating cancer which comprises administering a therapeutically effective amount of a compound of formula I, II, III or IV, and mixtures thereof, or pharmaceutically acceptable salts thereof in combination with a therapy selected from the group consisting of radiation therapy and chemotherapy.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

DETAILED DESCRIPTION OF THE PREFERRED EMBODIMENTS

The compounds of this invention are illustrated by a compound of Formula I or a pharmaceutically acceptable salt or stereoisomer thereof, wherein Formula I

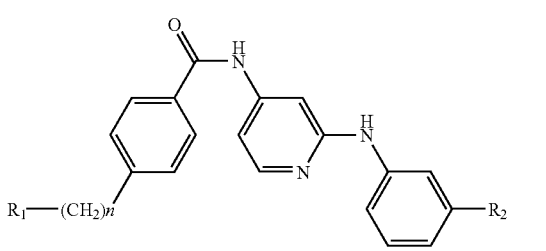

wherein n is an integer, preferably n is 1;

wherein $R_1$ and $R_2$ are independently selected from the group consisting of:

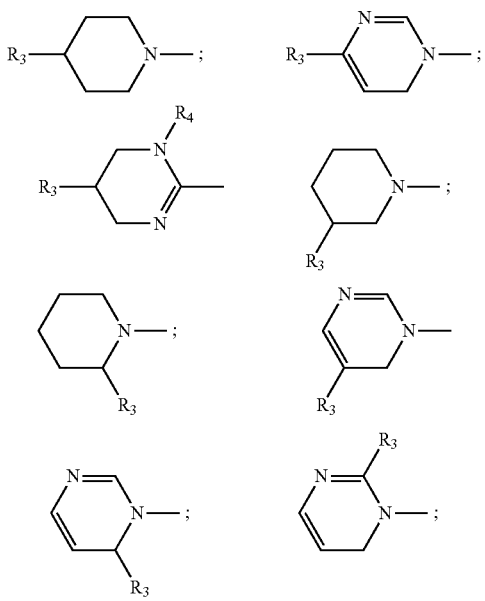

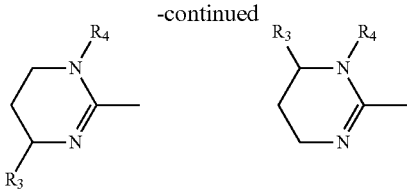

wherein $R_3$ is selected from the group consisting of H; alkyl; alkenyl; alkynyl; halogen; aryl; heteroaryl containing N, O, or S; the aryl and heteroaryl may be further substituted with halogen, an alkyl, alkenyl, and alkynyl; $NZ_1Z_2$, wherein $Z_1$ and $Z_2$ are independently selected from the group consisting of H and alkyl; and (CO)Y wherein Y is selected from the group consisting of H, alkyl, alkenyl, alkynyl, aryl, heteroaryl containing N, O, or S, and the aryl and heteroaryl may be further substituted with halogen, alkyl, alkenyl, and alkynyl; and wherein $R_4$ is selected from the group consisting of H and alkyl.

Yet another embodiment of the present invention is a compound which is selected from the group consisting of 4-(5-Methyl-1,4,5,6-tetrahydro-pyrimidin-2-ylmethyl)-N-{2-[3-(1,4,5,6-tetrahydropyriminin-2-yl)-phenylamino]-pyridin-4-yl}benzamide (Formula II), 4-(4-Amino-piperidin-1-yl) methyl-N-{2-[3-(6H-pyrimidin-1-yl)-phenylamino]-pyridin-4-yl}benzamide (Formula III) and 4-(4-Amino-piperidin-1-yl)methyl-N-{2-[3-(3,4,5,6-tetrahydropyrimidin-2-yl)-phenylamino]-pyridin-4-yl}benzamide (Formula IV) as well as pharmaceutically acceptable salts or stereoisomers thereof.

Using an in silico assay, the compounds of the present invention have been demonstrated and predicted to have in vitro activity against a variety of cancerous cell types, some data are shown in Table 1. Also, while not explicitly shown, compounds of Formula II, III and IV have predicted in vitro activity against HIV.

Included within the scope of the present invention is a pharmaceutical composition which is comprised of a compound of Formula I as described above and a pharmaceutically acceptable carrier. The present invention also encompasses a method of treating or preventing cancer in a mammal in need of such treatment which is comprised of administering to the mammal a therapeutically effective amount of a compound of Formula I. Preferred cancers for treatment are selected from cancers of the breast, colon, prostate, gastric, melanoma, ovarian and leukemias. Another preferred form of cancer is chronic myelogic leukemia (CML).

The invention also encompasses pharmaceutical compositions comprising a compound of Formula I, II, III and/or IV as well as pharmaceutically acceptable salts thereof for the treatment of HIV.

The compositions and methods of the invention can include a compound of Formula I, II, III or IV, or mixtures thereof, as desired.

Also included is a method of treating or preventing a tyrosine kinase-dependent disease or condition in a mammal which comprises administering to a mammalian patient in need of such treatment a therapeutically effective amount of a compound of Formula I. The therapeutic amount varies according to the specific disease and is discernible to the skilled artisan without undue experimentation.

Also included in the scope of the claims is a method of treating cancer which comprises administering a therapeutically effective amount of a compound of Formula I, Formula II, Formula III and Formula IV in combination with radiation therapy and/or in combination with a compound generally known for use in selected cancers and selected from the group consisting of an estrogen receptor modulator, an androgen receptor modulator, retinoid receptor modulator, a cytotoxic agent and an antiproliferative agent. These and other aspects of the invention will be apparent from the teachings contained herein.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include but are not limited to the proliferation of tumor cells.

The compounds of the present invention may have asymmetric centers, chiral axes, and chiral planes (as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

As used herein, "alkyl" is intended to include both branched, straight-chain, and cyclic saturated aliphatic hydrocarbon groups having the specified number of carbon atoms. For example, $C_1$-$C_{10}$, as in "$C_{1-10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydro-naphthalene, methylenecylohexyl, and so on. "Alkoxy" represents an alkyl group of indicated number of carbon atoms attached through an oxygen bridge.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to 4 non-aromatic carbon-carbon double bonds may be present. For instance, "$C_2$-$C_6$ alkenyl" means an alkenyl radical having from 2 to 6 carbon atoms. Alkenyl groups may include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to 3 carbon-carbon triple bonds may be present. For instance, "$C_2$-$C_6$ alkynyl" means an alkynyl radical having from 2 to 6 carbon atoms. Alkynyl groups may include ethynyl, propynyl and butynyl. As described above with respect to alkyl, the straight, branched or cyclic portion of the alkynyl group may contain triple bonds and may be substituted if a substituted alkynyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions and standard manipulations that are known in the literature or exemplified in the experimental procedures.

The compound of general formula I may be synthesized using a palladium-catalyzed coupling reaction as follows:

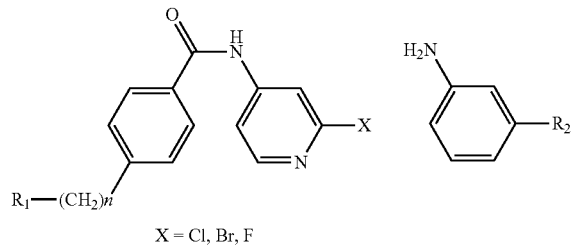

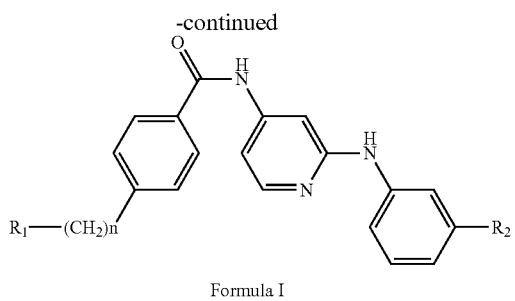

Formula I

Some suitable palladium coupling catalysts for promoting carbon-nitrogen bond-forming cross-coupling include, but are not limited to, Pd(OAc)$_2$ with BINAP (2,2'-bis(diphenylphosphino)-1,1'-binaphthyl) and Pd$_2$(dba)$_3$ (dba is diphenyl phosphine ferrocene) with DPPF (dibenzylidene acetone). Protecting groups may be utilized to protect the R$_1$ and R$_2$ groups during the coupling reaction and, as a result, a further step may include deprotection. As a result of deprotection, the salt of formula I may be formed. The free base may be obtained by treating the salt with a base such as, but not limited to, sodium hydroxide and sodium carbonate.

In an illustrative example, the salt of formula IV may be synthesized as shown in Scheme 1.

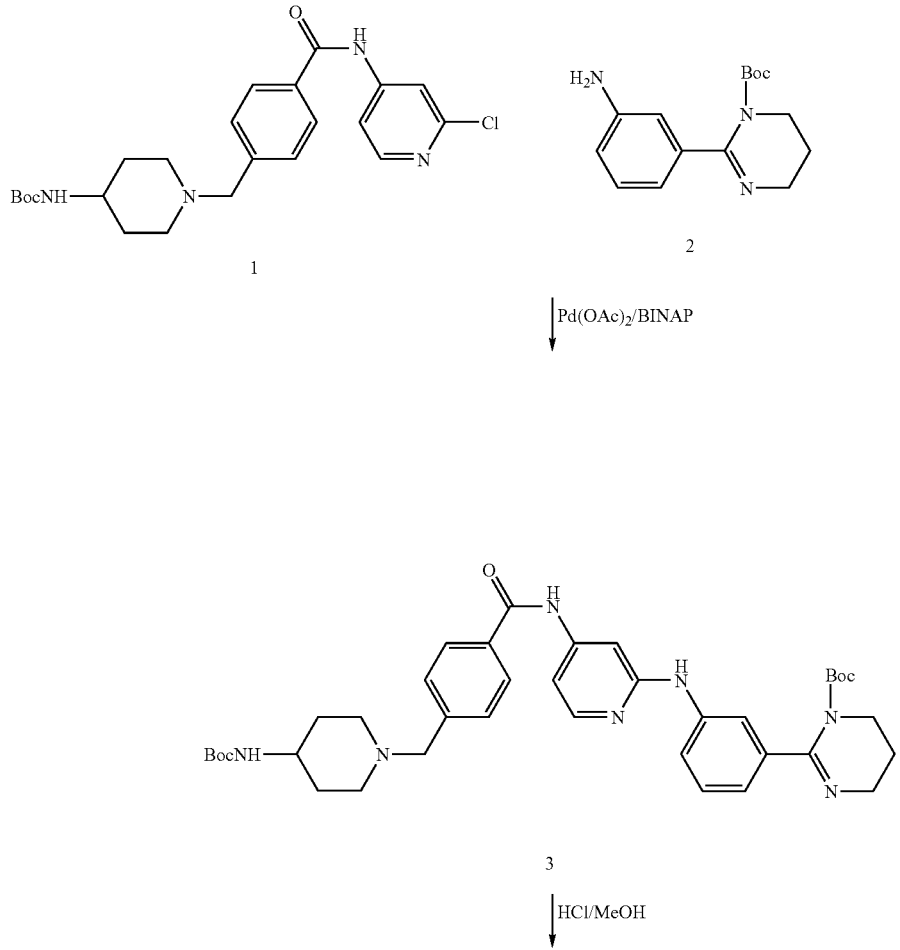

Scheme 1

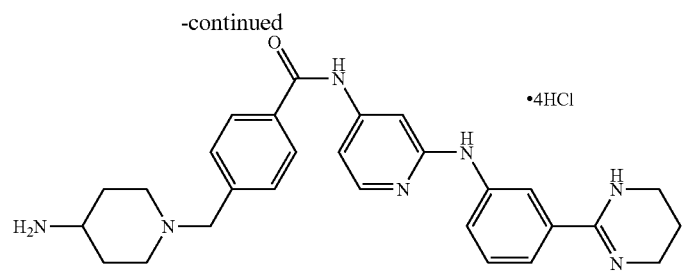

Salt of Formula IV

Intermediates 1 and 2 underwent a coupling reaction in the presence of Pd(OAc)$_2$ and BINAP to yield the Boc-protected coupling product 3. The Boc protective groups were removed with saturated HCl solution in MeOH to afford the salt of Formula IV.

Intermediates for the coupling reaction may be prepared using various reactions known in the literature. For instance, intermediate 1 may be synthesized as shown in Scheme 2.

Scheme 2

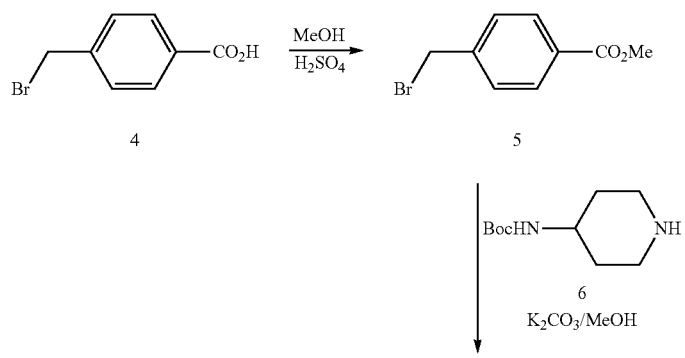

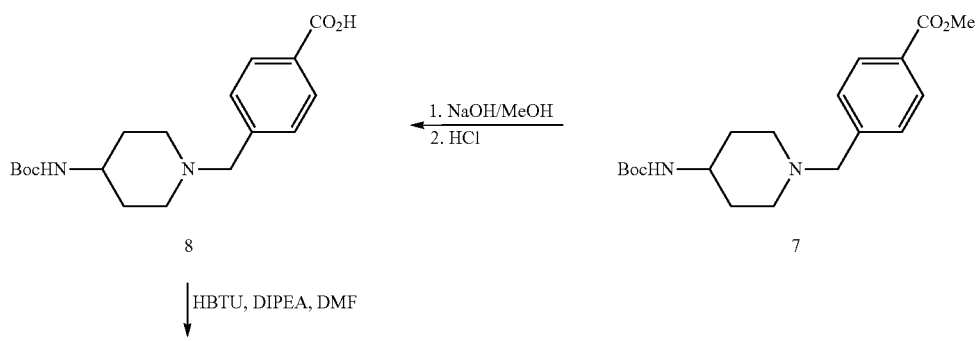

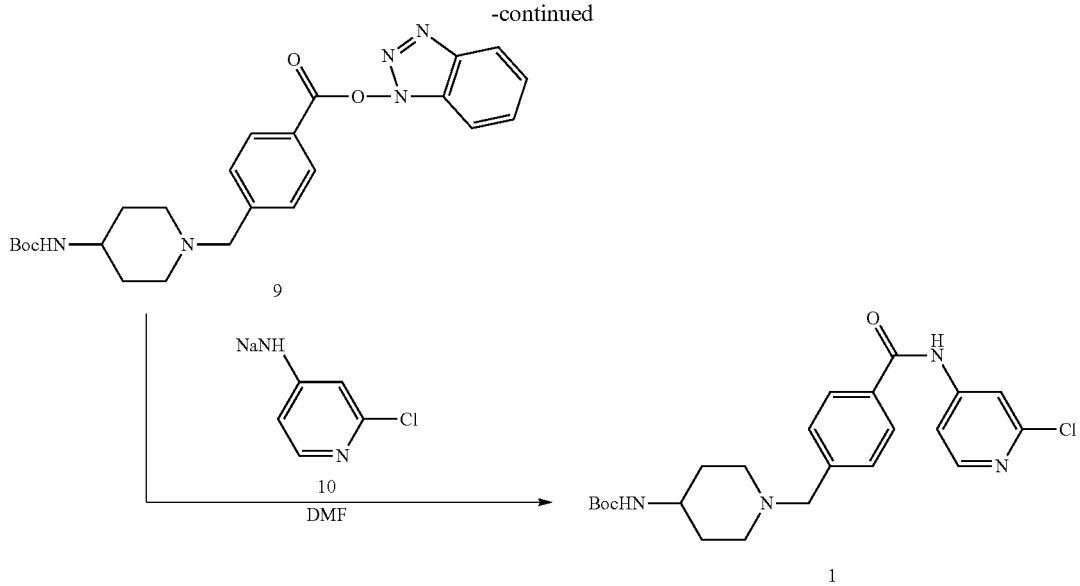

The first step for synthesizing intermediate 1 involved the esterification of 4-bromomethylbenzoic acid 4 to methyl 4-bromomethylbenzoate 5. Methyl 4-bromomethylbenzoate 5 was then reacted with commercially available 4-boc-aminopiperidine 4 to yield compound 7. The ester group of compound 7 was hydrolyzed to compound 8 and further reacted with coupling reagent, HBTU, and DIPEA in DMF to form the activated ester 9. The activated ester 9 was then reacted with sodium 2-chloropyrid-4-ylamide 10 to yield intermediate 1.

Intermediate 2 may be synthesized as shown in Scheme 3.

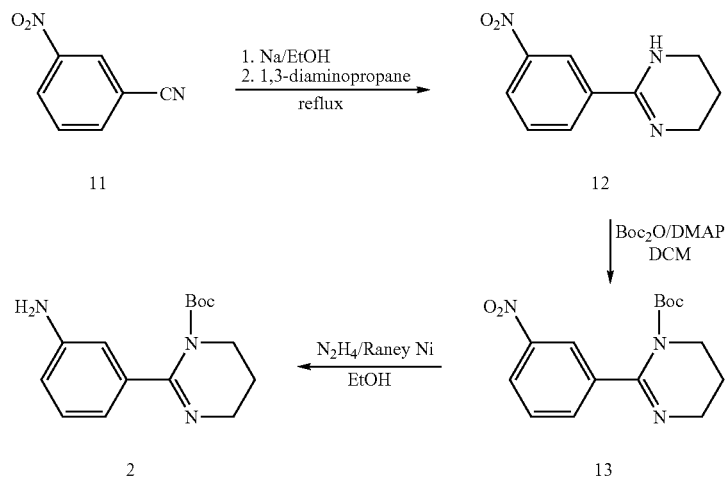

For the transformation of 3-nitrobenzonitrile 11 into 3,4,5,6-tetrahydro-2-(3-nitrophenyl)-pyrimidine 12 was conducted using a procedure described in European Patent Application 0225726 A1 for 4-nitrobenzonitrile; incorporated herein by reference. 3,4,5,6-tetrahydro-2-(3-nitrophenyl)-pyrimidine 12 was protected using $Boc_2O$, carried out in DCM at room temperature in the presence of DMAP as a catalyst to yield Boc-protected compound 13, which was then reduced to intermediate 2.

In a further example, the salt of formula III may be synthesized as shown in Scheme 4, which is similar to the reaction shown in Scheme 1.
Intermediate 14 may be synthesized as shown in Scheme 5.
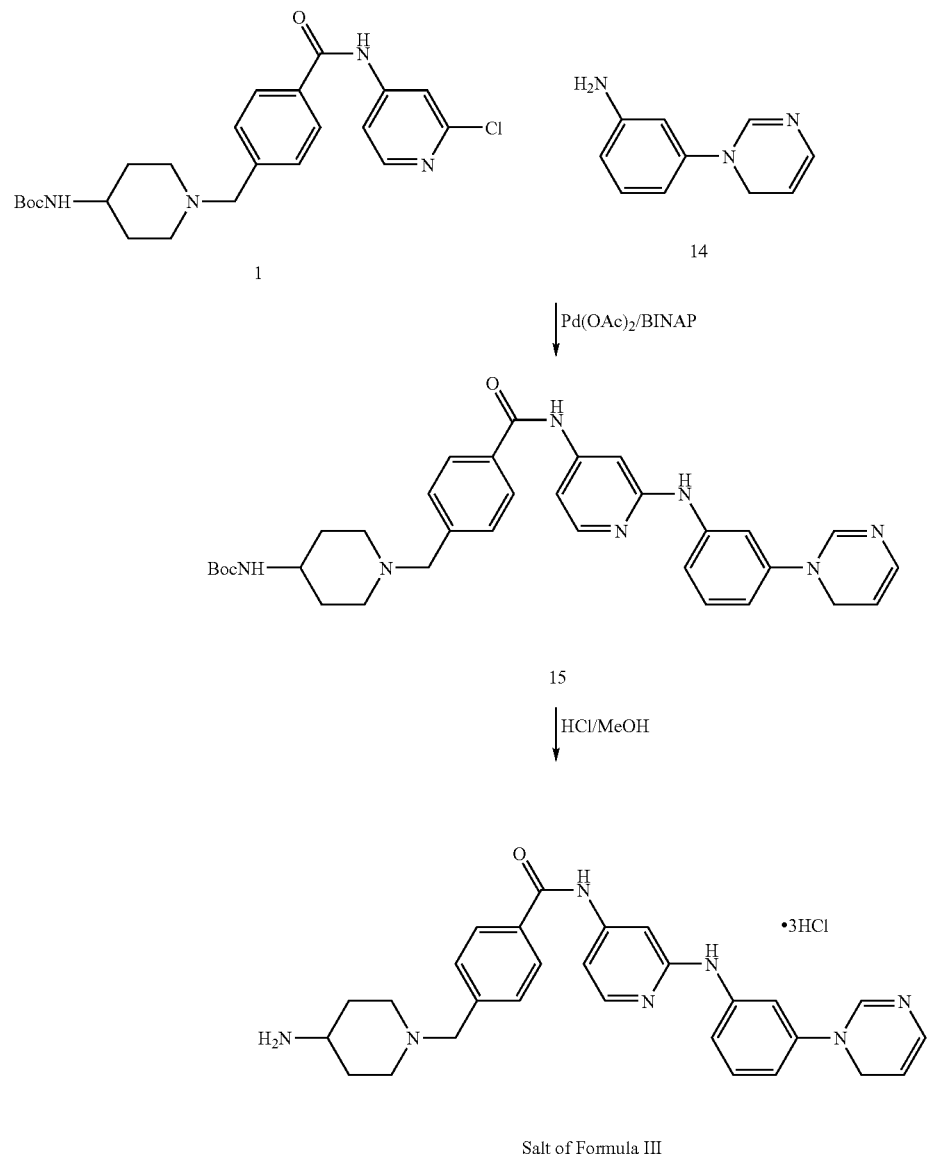
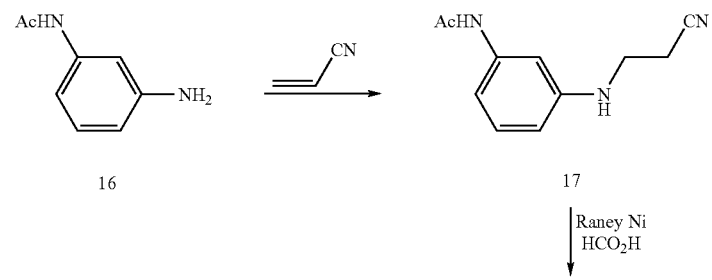

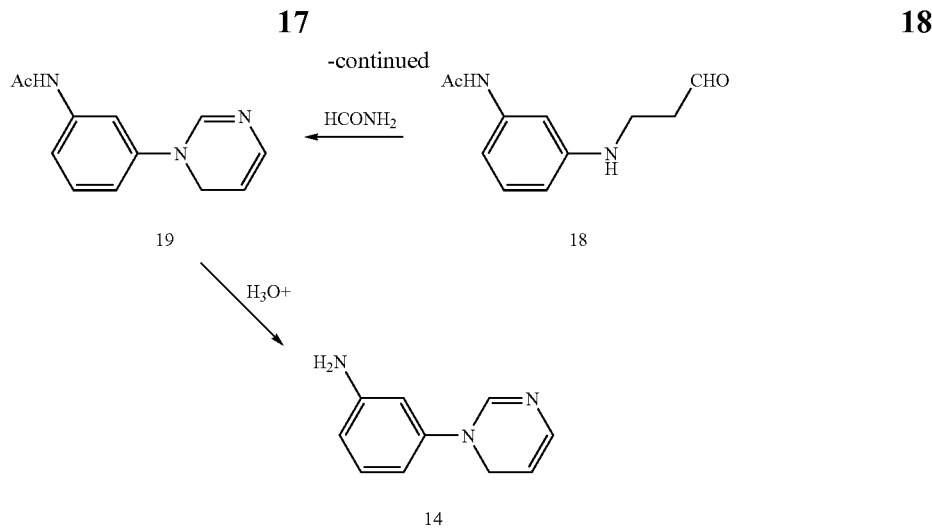

The reaction of 3'-aminoacetanilide 16 with acrylonitrile yields the resultant addition product 17. Reduction of the addition product 17 yields the aldehyde 18. The aldehyde 18 reacts with formamide to yield the cyclic compound 19. The cyclic compound 19 is then hydrolyzed to intermediate 14.

The compounds of the instant invention are useful as pharmaceutical agents for mammals, especially for humans, in the treatment of tyrosine kinase dependent diseases and in particular the treatment of various cancers.

The compounds of the instant invention may be administered to patients for use in the treatment of cancer.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadministered with radiation therapy. The synergistic effects of inhibiting VEGF in combination with radiation therapy have been described in the art. (see WO 00/61186). "Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl) retinamide and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunor-ubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(-3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methy-1H,12H benzo[de]pyrano[3',4':b,7]indolizino[1,2b]quinoline-10,13(9H,15H) dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazo-le-1-carboxamide, asulacrine, (5a, 5aB, 8aa,9b)-9-[2-[N-[2-(dimethylamino)-ethyl]-N-methylamino]ethyl]-5-[4-Hydroxy-3,5-dimethoxyphenyl]-5,5a,6, 8,8a,-9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridiniu-m, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-py-razolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2-,1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydrobenzofuryl)sulfonyl]-N'-(3,4-dichlorophenyl) urea, N6-[4-deoxy-4-[N2-[2(E),4(E)-tetradecadienoyl]glycylamino]-L-glycer-o-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino-)-7-methoxy-6-[3-(4-morpholinyl)propoxyl]quinazoline, N-(3-ethynylphenyl)-6, 7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2', 1'-kl]pyrrolo[3,4-i][1,6]benzodiazocin-1-one, SH1382, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)-amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, particularly cancers involving inappropriate tyrosine kinase activity, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Methods of synthetic chemistry, protein and peptide biochemistry, molecular biology, and pharmacology referred to but not explicitly described in this disclosure and examples are reported in the scientific literature and are well known to those skilled in the art.

Example 1

Molecules with the potential target biological activity were analyzed in a validated in silico assay that is based on public domain National Cancer Institute in vitro anti-cancer data. The molecules are first decomposed to 110 descriptors using a proprietary CHEMSAS™ algorithm. This decomposition process results in a molecular data pattern of 110 variables that is then input into the in silico model. The output of the model is a prediction of the –Log(GI50) for the molecule(s) being analyzed against the specific cancer cell type in question i.e. breast cancer or leukemia, etc. A specific in silico assay was also developed for the leukemia cell line (i.e. K562) that over expresses the abnormal protein tyrosine kinase found in Chronic Myelogenous Leukemia (CML). Results of the in silico assay for molecular Formulas II and III in a number of cancer cell types are summarized below in Table 1.

TABLE 1

| Compound | leukemia | K562 (CML)* | NSCLC** | SCLC*** | Colon | CNS |
|---|---|---|---|---|---|---|
| Formula II | −5.41 | −5.66 | −4.97 | −4.79 | −5.12 | −5.02 |
| Formula III | −5.43 | −5.76 | −5.04 | −4.73 | −5.3 | −5.05 |
| Formula IV | | −5.7 | | | | |

| Compound | Melanoma | Ovary | Renal | Prostate | Breast |
|---|---|---|---|---|---|
| Formula II | −4.91 | −5.0 | −4.91 | −5.17 | −4.75 |
| Formula III | −4.95 | −4.99 | −4.97 | −5.86 | −4.84 |

Note:
Values in the table refer to the –Log(GI50) as a molar concentration.
If –Log(GI50) > −4.5 then the compound is likely to be inactive.
If –Log(GI50) > −5 and <−4.5 then the compound is likely to have some in vitro activity.
If –Log(GI50) < −5 then the compound is considered to have in vitro activity.
*K562 is a specific leukemia cell line for CML that over expresses the abnormal protein tyrosine kinase.
**NSCLC is a non small cell lung cancer
***SCLC is a small cell lung cancer Example 2

Synthesis of the Salt of Formula IV

Intermediate 1

Intermediate 1 was prepared as shown in Scheme 2. Esterification of 4-bromomethylbenzoic acid 4 (25 grams) was carried out in refluxing methanol (500 ml) in the presence of concentrated $H_2SO_4$ (5 ml) to yield methyl 4-bromomethylbenzoate 5. TLC (thin layer chromatography) monitoring of the reaction mixture showed formation, over time, of a side-product (about 15-20%), which according to $^1$H-NMR analysis, was identified as methyl 4-methoxymethylbenzoate. The mixture of methyl 4-bromomethylbenzoate 5 and the side-product (4.56 grams; 1 equiv) was reacted with commercially available 4-boc-aminopiperidine 6 (Aldrich™) (4.0 grams) in 100 ml of DCM or 100 ml of methanol in the presence of potassium carbonate (4.14 grams; 1.5 equiv) at room temperature to yield compound 7. Reaction in methanol afforded compound 7, as identified by $^1$H NMR, in 72% yield compared to 57% obtained with DCM.

Compound 7 was refluxed with NaOH (1.5 eq) in methanol for 4-5 hours. The reaction mixture was cooled and 2.0 M HCl solution in ether was added to neutralize excess NaOH and convert the corresponding sodium carboxylate into the free acid. Then solvent was carefully removed in vacuum and the residue treated with water/DCM 1:1. Pure 8 crystallized at the water/DCM interface as a white solid, which was collected by filtration and air dried to give an 83.7% yield.

A mixture of 8 (1 gram, (1.0 equiv)), HBTU (O-Benzotriazole-N,N,N',N'-tetramethyl-uronium-hexafluoro-phosphate) (1.36 grams, (1.2 equiv)), DIPEA (N,N-diisopropylethylamine) (1.6 ml (3 equiv)) and DMF (dimethylformamide) (30 ml) was stirred at room temperature for four hours to form the activated ester 9 (42% yield). 2 equivalents of sodium 2-chloropyrid-4-ylamide (generated from the reaction of 4-amino-2-chloropyridine with sodium hydride) in DMF was added. The reaction mixture was stirred for 5 hours at room temperature and separated by preparative TLC, and identified by $^1$H NMR and MS as intermediate 1.

Intermediate 2

Intermediate 2 was prepared as shown in Scheme 3. For the transformation of 3-nitrobenzonitrile 11 into 3,4,5,6-tetrahydro-2-(3-nitrophenyl)-pyrimidine 12 (25% yield), a procedure described in European Patent Application 0225726 A1 (incorporated herein by reference) for 4-nitrobenzonitrile was used. 3-nitrobenzonitrile 11 (21 grams), sodium (0.32 grams, 0.1 equiv), diaminopropane (12 ml) and 190 ml of anhydrous ethanol was used. 3,4,5,6-tetrahydro-2-(3-nitrophenyl)-pyrimidine 12 (30 grams) was protected using $Boc_2O$ (di-tert-butyl dicarbonate) (38 grams; 1.2 equiv), carried out in DCM (1.4 ml) at room temperature in the presence of DMAP (4-dimethylaminopyridine) (0.9 grams; 0.05 equiv) as a catalyst to yield Boc-protected compound 13 (76% yield). The nitro group of compound 13 (21 grams) was reduced with a hydrazine hydrate (13.4 ml; 4.0 equiv)/Raney Ni (25 grams) system in 350 ml of ethanol at 50-75° C. for about 30 minutes, which afforded Intermediate 2 in a 47% yield.

Salt of Formula IV

The salt of Formula IV was prepared as shown in Scheme 1. A mixture of 9 grams of intermediate 1 and 5.4 grams of intermediate 2 was prepared. 30 mol % $Pd(OAc)_2$ and 45 mol % BINAP (2,2'-bis(diphenyphosphino)-1,1'-binaphthyl) were employed in the reaction. After heating the reaction mixture for about 20 hours, the reaction was then worked up. In order to get rid of all non-basic impurities, and therefore diminish the amount of crude material needed to be purified, the reaction mixture was diluted with EtOAc and extracted with 5% HCl solution. The substrates and final product were separated into the acidic aqueous phase. The acidic phase was then neutralized with NaOH and basic components extracted with EtOAc. Concentration of the extracts afforded 13 g crude mixture in total. Compound 3 was separated using column chromatography (5-10% MeOH in DCM) to provide us with 0.9 g (6.5% yield) pure amide 3. Finally, the Boc protective groups were removed using a saturated HCl solution in MeOH and the HCl salt of Formula IV was precipitated out with anhydrous ether to afford 0.58 g (70% yield).

Although the $^1$H-NMR spectrum of the HCl salt of Formula IV compared to that of compound 3, the mass-spectrum of the HCl salt of Formula IV showed a single signal of the protonated molecular ion [M+H$^+$]=484 which corresponds to the free base of Formula IV.

Although preferred embodiments of the invention have been described herein in detail, it will be understood by those skilled in the art that variations may be made thereto without departing from the spirit of the invention.

We claim

1. A compound selected from the group consisting of a compound of Formula I, a pharmaceutically acceptable salt thereof and a stereoisomer thereof:

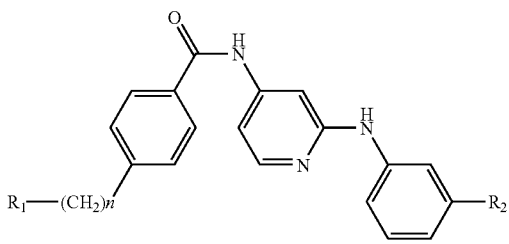

Formula I wherein n is 0;

wherein $R_1$ and $R_2$ are independently selected from the group consisting of:

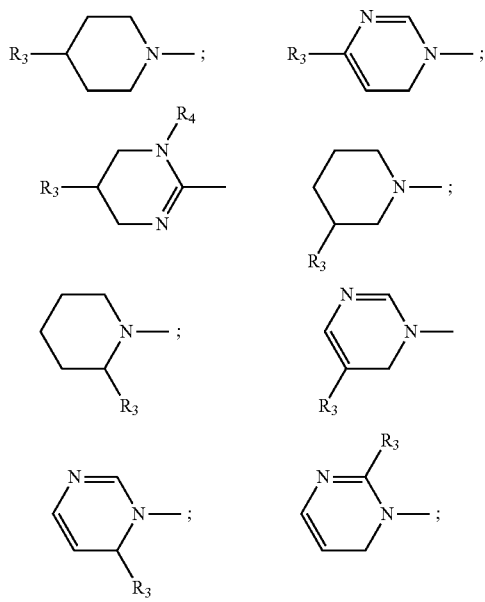

-continued

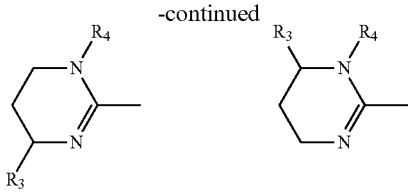

wherein $R_3$ is selected from the group consisting of H; alkyl; alkenyl; alkynyl;

halogen; aryl; heteroaryl containing N, O, or S; $NZ_1Z_2$, wherein $Z_1$ and $Z_2$ are independently selected from the group consisting of H and alkyl; and (CO)Y wherein Y is selected from the group consisting of H, alkyl, alkenyl, alkynyl, aryl, heteroaryl containing N, O, or S; and wherein $R_4$ is selected from the group consisting of H and alkyl.

2. The compound of claim 1, wherein the aryl and heteroaryl are substituted with at least one of a halogen, an alkyl, an alkenyl, and an alkynyl.

3. The compound of claim 1, wherein the pharmaceutically acceptable salt is derived from an inorganic acid or an organic acid, wherein the inorganic acid is selected from the group consisting of hydrochloric, hydrobromic, sulfuric, sulfamic, phosphoric, and nitric acids; and the organic acid is selected from the group consisting of acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, and trifluoroacetic acids.

4. The compound of claim 3, wherein the pharmaceutically acceptable salt is derived from hydrochloric acid.

5. A pharmaceutical composition comprising the compound of claim 1 or mixtures thereof, and a pharmaceutically acceptable carrier.

6. A method for making the compound of claim 1, comprising reacting

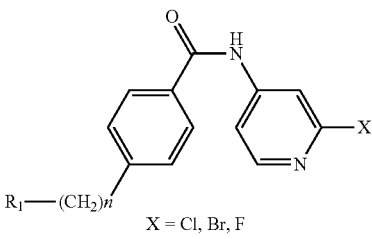

X = Cl, Br, F

With

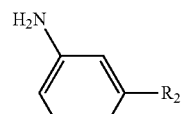

in the presence of a palladium coupling catalyst for promoting carbon-nitrogen bond-forming cross-coupling.

7. The method of claim 6, wherein the palladium coupling catalyst is one of Pd(OAc)$_2$ with BINAP and Pd$_2$(dba)$_3$ with DPPF.

8. The method of claim 6, wherein the $R_1$ and/or $R_2$ groups contain protecting groups and the method further comprises a deprotection step.

9. A method of treating a tyrosine kinase-dependent cancer in a mammal in need of such treatment, wherein the cancer is selected from the group consisting of breast, colon, ovarian, prostate, chronic myelogic leukemia (CML), acute leukemias, melanoma, CNS and lung, comprising administering to the mammal a therapeutically effective amount of the compound of claim 1 or mixtures thereof.

10. The method of claim 9, wherein the therapeutically effective amount is between about 0.1 mg/kg of body weight to about 60 mg/kg of body weight per day.

11. The method of claim 10, wherein the therapeutically effective amount is between about 0.5 mg/kg of body weight to about 40 mg/kg of body weight per day.

12. The method of claim 9 further comprising a therapy selected from the group consisting of radiation therapy and chemotherapy.

13. The method of claim 12, wherein the therapeutically effective amount is between about 0.1 mg/kg of body weight to about 60 mg/kg of body weight per day.

14. The method of claim 13, wherein the therapeutically effective amount is between about 0.5 mg/kg of body weight to about 40 mg/kg of body weight per day.

15. The method of claim 9, wherein the cancer is chronic myelogic leukemia (CML).

16. A process for making a pharmaceutical composition which comprises combining a compound of claim 1 or mixtures thereof, with a pharmaceutically acceptable carrier.

17. A composition comprising a compound of claim 1 or mixtures thereof, and a compound selected from the group consisting of an estrogen receptor modulator, an androgen receptor modulator, a retinoid receptor modulator, a cytotoxic agent, an anti-proliferative agent, a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-$\alpha$, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, tamoxifen and raloxifene.

* * * * *

UNITED STATES PATENT AND TRADEMARK OFFICE
CERTIFICATE OF CORRECTION

PATENT NO.       : 8,252,800 B2
APPLICATION NO.  : 12/510862
DATED            : August 28, 2012
INVENTOR(S)      : Wayne R. Danter et al.

It is certified that error appears in the above-identified patent and that said Letters Patent is hereby corrected as shown below:

Title page, item (73) add: Assignee: Critical Outcome Technologies, Inc., Ontario, Canada Signed and Sealed this
Seventeenth Day of December, 2013

Margaret A. Focarino
*Commissioner for Patents of the United States Patent and Trademark Office*